United States Patent [19]

Chalvignac

[11] Patent Number: 5,542,416
[45] Date of Patent: Aug. 6, 1996

[54] APPARATUS FOR ASSISTING VENTILATION INCLUDING REDUCED EXHALATION PRESSURE MODE

[75] Inventor: Philippe Chalvignac, Noisy Sur Ecole, France

[73] Assignee: Societe d'Applications Industrielles Medicales Et Electroniques (SAIME), Savigny Le Temple, France

[21] Appl. No.: 370,636

[22] Filed: Jan. 10, 1995

[30] Foreign Application Priority Data

Jan. 12, 1994 [FR] France .................... 94 00246

[51] Int. Cl.⁶ .................... A61M 16/00; A61M 16/20
[52] U.S. Cl. .................... 128/204.23; 128/205.24; 128/204.25
[58] Field of Search .................... 128/204.23, 204.21, 128/204.19, 204.18, 204.25, 205.24, 205.25; 137/560, 625.5, 625.27, 625.65

[56] References Cited

U.S. PATENT DOCUMENTS

| | | | |
|---|---|---|---|
| 3,831,596 | 8/1974 | Cavallo | 128/204.23 |
| 3,935,880 | 2/1976 | Lindestrom et al. | 137/499 |
| 3,985,131 | 10/1976 | Buck et al. | 128/204.23 |
| 4,401,115 | 8/1983 | Monnier | 128/204.23 |
| 4,773,411 | 9/1988 | Downs | 128/204.18 |
| 4,838,257 | 6/1989 | Hatch | 128/204.18 |
| 5,000,173 | 3/1991 | Zalkin et al. | 128/204.21 |

FOREIGN PATENT DOCUMENTS

| | | | |
|---|---|---|---|
| 888520 | 12/1971 | Canada | 128/204.19 |
| 0317417 | 5/1989 | European Pat. Off. . | |
| 0347015 | 12/1989 | European Pat. Off. . | |
| 0425092 | 5/1991 | European Pat. Off. . | |
| 0459647 | 12/1991 | European Pat. Off. . | |
| 0549299 | 6/1993 | European Pat. Off. . | |
| 2422885 | 12/1979 | France | 137/625.5 |
| 2682042 | 4/1993 | France . | |
| 2045929 | 3/1972 | Germany | 137/625.5 |
| 2604006 | 8/1977 | Germany | 137/560 |
| 8910768 | 11/1989 | WIPO . | |
| 9406499 | 3/1994 | WIPO . | |

Primary Examiner—V. Millin
Assistant Examiner—Eric P. Raciti
Attorney, Agent, or Firm—Plevy & Associates

[57] ABSTRACT

The invention provides apparatus for assisting with the ventilation of a patient, which includes a source (10) of pressurized gas, a transmission circuit including a main inhalation conduit (14) connected to a mask (19) worn by the patient (20), and a secondary exhalation conduit (28), a flow regulating valve (16), and an exhalation valve (30), characterized in that the regulating valve (16) includes means (52) for maintaining a residual flowrate under a reduced pressure in the main inhalation conduit (14) during each exhalation phase.

16 Claims, 4 Drawing Sheets

APPARATUS FOR ASSISTING VENTILATION INCLUDING REDUCED EXHALATION PRESSURE MODE

FIELD OF THE INVENTION

The present invention relates to apparatus for assisting with the ventilation of a patient.

BACKGROUND OF THE INVENTION

The invention relates more particularly to an apparatus for assisting with the ventilation of a patient who is breathing with successive cycles, each of which includes an inhalation phase and an exhalation phase, of the type especially including an inhalation assistance mode during which the apparatus delivers to the patient, during the inhalation phase triggered by the beginning of inhalation of the patient, a flowrate of gas under a pressure equal to a given reference value and which includes:

a source of pressurized gas, an outlet orifice of which delivers a flowrate of pressurized gas intended to be transmitted to the upper airways of the patient;

a transmission circuit including a main inhalation conduit connected to the outlet orifice of the source of pressurized gas and to a mask, especially of the face mask type, intended to be worn by the patient, and including a secondary exhalation conduit connected to the mask and to a discharge orifice;

a flow regulating valve which is interposed in the main conduit and which is operated by an operating circuit of the apparatus on the basis especially of the values of the flowrate and of the pressure of the gas in the main inhalation conduit measured downstream of the regulating valve, especially in order to determine the beginning of the inhalation phase; and an exhalation valve interposed in the secondary exhalation conduit which is made to open by the operating circuit of the apparatus, especially during the exhalation phase of each breathing cycle of the patient in respiratory aid mode.

An example of such a type of apparatus is illustrated in the documents WO-A-89 10768 and EP-A-0,425,092.

When it is used in inhalation assistance mode, all of the flowrate of pressurized gas, especially pressurized air, is transmitted to the mask (worn by the patient) during each inhalation phase, the exhalation valve being closed.

During each exhalation phase, the exhalation valve is open and the inlet orifice of the mask to which the main conduit is connected is thus vented to ambient air so that the patient can freely exhale the air inhaled during the previous inhalation phase.

During this exhalation phase, the function of the flow regulating valve is to interrupt the flowrate in the main inhalation conduit by bypassing, for example, the flow of pressurized air produced by the source to outside the apparatus.

The flow regulating valve must thus allow a relative pressure at the inlet of the mask, during the exhalation phase, which is predetermined and may be close to zero.

The operating circuit detects the exhalation phase of the patient when the pressure measured in the main conduit is greater than a reference value or when the flowrate of this conduit drops below a reference threshold value.

A classic design of the regulating valve described in document WO-A-89 10768 is such that operation of the valve of "all-or-nothing" type involves the use of an axial compressor as a source of pressurized air.

In this document, the variation in air pressure is here effectively obtained by causing the rotational speed of the compressor to vary, which requires several respiratory cycles to establish a determined value for the pressure.

What is more, that gives rise to noises of acceleration and deceleration of the motor of the compressor which are particularly troublesome in the case of a home respiratory-aid apparatus.

In document EP-A-0,425,092, the ventilator described and represented is connected to a mask for supplying pressurized air which is equipped with ventilation openings which allow both the exhalation and the passage of a residual flowrate into the supply circuit.

These openings, which may or may not be equipped with a check valve, must be sufficiently large to allow the exhaled gases to be discharged, even under a low exhalation pressure.

In contrast, their size is limited by the need to have a reduced leakage flowrate, which necessarily means that exhalation cannot take place at a very low pressure.

The application of the principle described in this document implemented commercially by the RESPIRONICS company is known under the trade name of BIBAP Ventilatory Support System.

This apparatus does not make it possible to have an exhalation pressure (EPAP) less than 4 mbar, which may constitute a hindrance for the patient.

The object of the invention is to provide an apparatus for aiding the ventilation of the type mentioned previously which overcomes the drawbacks which have just been outlined.

SUMMARY OF THE INVENTION

An apparatus for assisting ventilation of a patient characterized in that the flow regulating valve includes means for maintaining a residual flowrate under a pressure close to zero in the main inhalation conduit during each exhalation phase.

According to other characteristics of the invention:

the regulating valve includes a valve body which delimits a regulating chamber connected to an orifice for supplying with pressurized gas, to an orifice for delivering the pressurized gas into the main inhalation conduit, and to an orifice for venting to ambient air operated by a main check valve which is normally closed and the opening of which is brought about by a member for causing the movements of the check valve in order to vary the passage cross section of the orifice for venting to ambient air, and in that it includes a secondary check valve whose movements are connected to those of the main check valve and which, in the wide open position of the main check valve, partially shuts off the delivery orifice of the valve in order to determine the value of the residual flowrate under a pressure close to zero or equal to zero;

the main and secondary check valves are carried by a common operating rod connected to an actuating electromagnet whose electrical power supply is operated by the operating circuit of the apparatus;

the regulating valve has an axial tubular baffle which reduces and shifts towards the high frequencies, the noise spectrum resulting from the flow of gas;

the axial tubular baffle has a substantially conical end which, during exhalation, produces a venturi effect allowing the pressure of the residual flowrate to be reduced;

the exhalation valve is a valve which is normally closed, which is made to open by the operating circuit of the apparatus;

the exhalation valve is a pneumatically-operated valve supplied by a distributor controlled by the operating circuit;

the distributor includes one inlet connected to the outlet of the source of pressure where a high pressure prevails, one outlet connected to the exhalation valve and two positions, open or closed;

the distributor has two inlets, one connected to the outlet of the source of pressure where a high pressure prevails, the other to the inlet of the source of pressure where a partial vacuum prevails, one outlet connected to the exhalation valve and three positions, closed, and open to one or other of the two inlets;

the exhalation valve receives, in parallel with the distributor, a pressure signal which comes from the outlet chamber of the regulating valve;

the secondary exhalation conduit is connected in bypass on the main inhalation conduit downstream of the flowrate-measuring means;

the source of pressurized gas is a fan with a substantially constant speed of rotation;

the value of the flowrate in the main conduit is measured by a differential sensor;

the value of the pressure of the residual flowrate is less than 4 mbar and is preferably substantially equal to 1 mbar.

BRIEF DESCRIPTION OF THE DRAWINGS

Other characteristics and advantages of the invention will emerge during reading of the detailed description which will follow, for the understanding of which reference will be made to the appended drawings in which.

DETAILED DESCRIPTION OF THE INVENTION

Figure 1:
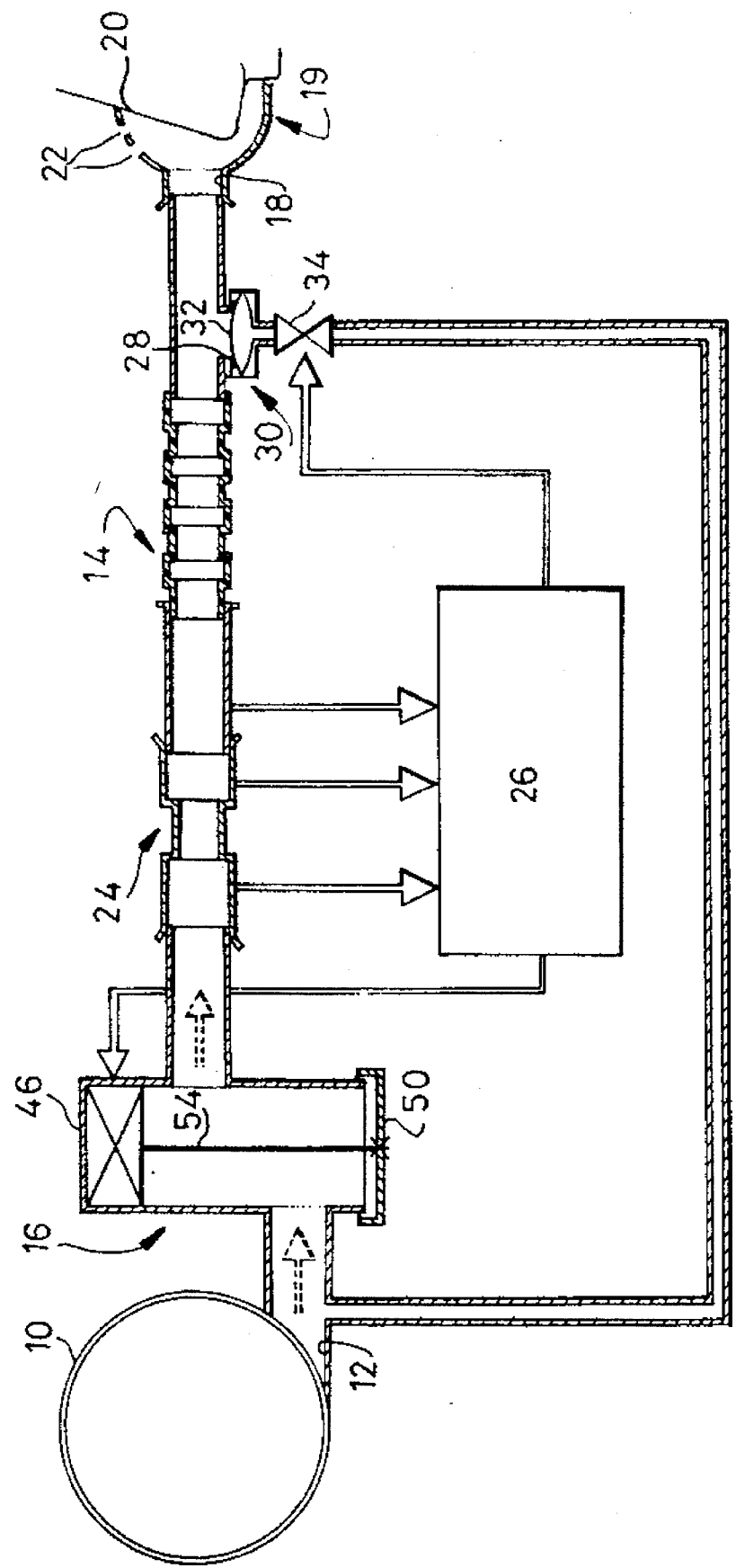
FIG. 1 is a diagrammatic view illustrating the design of an apparatus in accordance with the teachings of the invention and which is illustrated in the inhalation phase.
Figure 2:
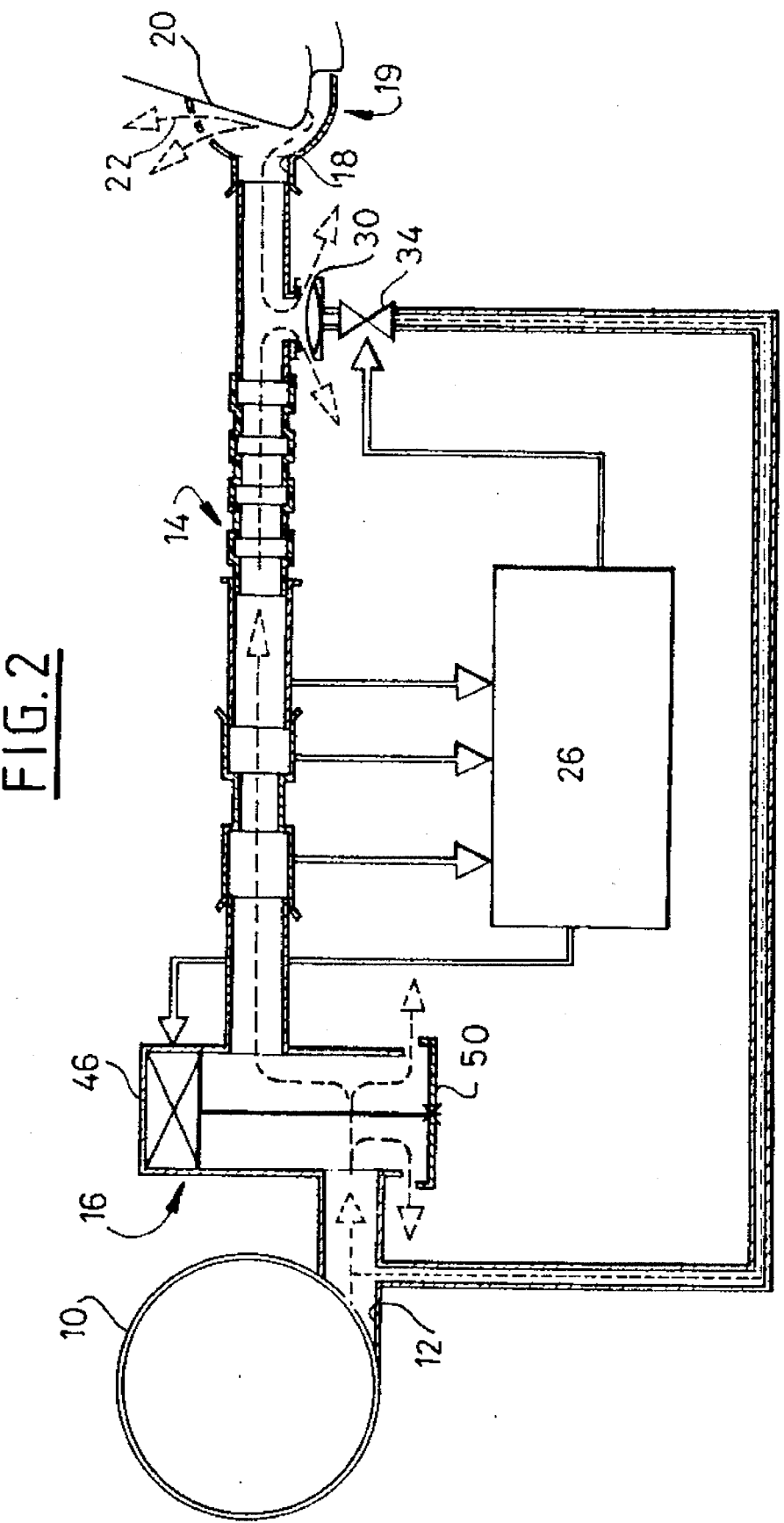
FIG. 2 is a view similar to that of FIG. 1 in which the apparatus is illustrated in the exhalation phase.
Figure 4:
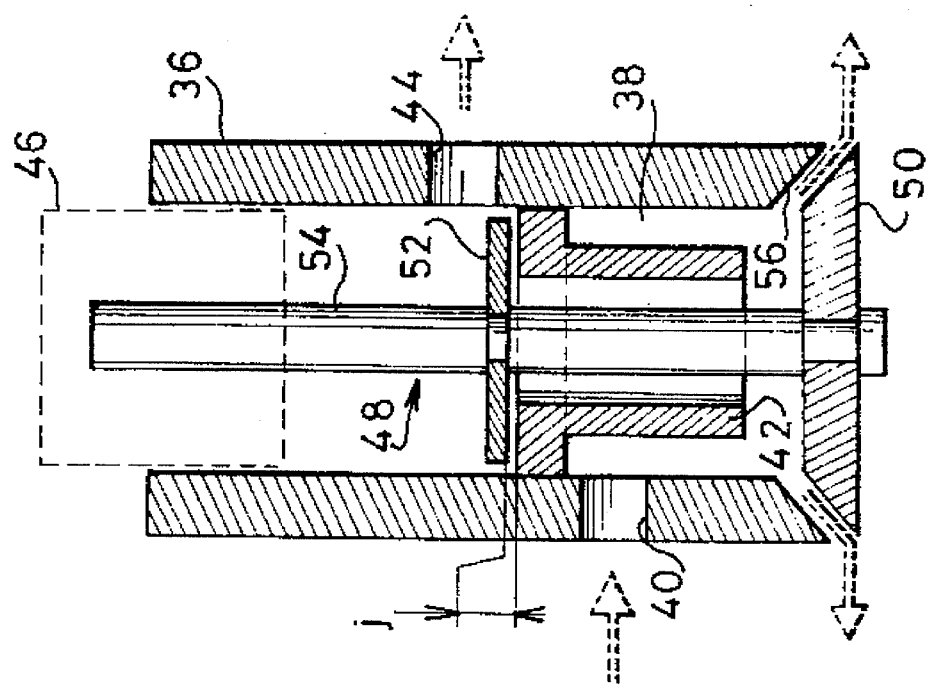
FIG. 4 is a view similar to that of FIG. 3 in which the valve is illustrated in a position which it occupies in the exhalation phase.
Figure 3:
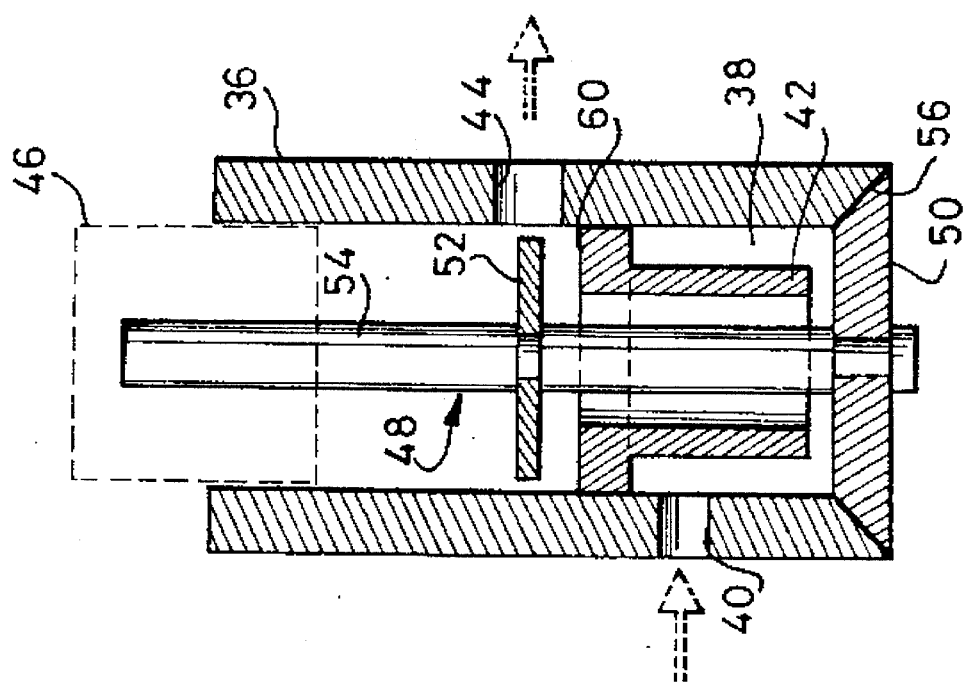
FIG. 3 is a diagrammatic view in section of one embodiment of a flow regulating valve illustrated in a position which it occupies in the inhalation phase.

The apparatus illustrated in FIGS. 1 and 2 includes a centrifugal fan-type compressor 10 which produces a flowrate of pressurized air, the fan 10 being, for example, one with a substantially constant rotational speed.

The outlet orifice 12 of the fan 10 is connected to a main inhalation conduit 14 with interposition of a flow regulating valve 16.

The main conduit 14 is connected to the inlet 18 of a face mask 19 worn by a patient 20 and which includes a series of openings 22, also known as "anti-rebreathing" openings.

A differential sensor 24 for measuring flowrate and pressure in the inhalation conduit 14 is interposed in the latter downstream of the flow regulating valve 16. The sensor 24, of a conventional design, transmits signals representing measured values of the pressure and of the flowrate to an electronic circuit 26 for operating the apparatus.

The apparatus also includes a main exhalation conduit 28 which is connected as a bypass on the main conduit 14 downstream of the valve 16 and close to the inlet 18 of the mask 19.

A pneumatically operated valve 30 is interposed in the secondary exhalation conduit 28.

In the example illustrated in FIGS. 1 and 2, the valve 30 is of the type which is pneumatically operated via a line for supplying it with pressurized air 32 which is permanently connected to the fan 10 and which inflates a shut-off balloon 33.

The valve 30 is operated by a distributor 34 interposed in the supply line 32 upstream of the valve 30 and which is operated by the operating circuit 26.

The operating circuit 26 also pilots the flow regulating valve 16 whose design according to the invention is as follows.

The valve 16 includes a valve body 36 which delimits a regulating chamber 38 into which there emerges a supply orifice 40 connected to the outlet 12 of the fan 10.

The chamber 38 in which a fixed baffle 42 is located is connected to the main conduit 14 via its delivery orifice 44.

The valve 16 includes an electromagnet 46, whose power supply is operated by the circuit 26 and which acts on a moving valve element 48 mounted so it can slide in the body 36 and which carries a main check valve 50 and a secondary check valve 52 which are integral with an operating rod 54 connected to the moving core plunger (not represented) of the electromagnet.

The function of the check valve 50 is to shut off totally or partially a discharge orifice 56 formed at the bottom of the chamber 38 and which communicates with the ambient air.

The function of the secondary check valve 52, in the exhalation phase, is to maintain a reduced passage cross section between the chamber 38 and the delivery orifice 44, so as to ensure a small residual flowrate at reduced pressure in the main inhalation line 14.

To this end, the secondary check valve 52 situated upstream of the orifice 44 maintains a radial clearance "j" with its seating 60 formed on the baffle 40, while the main check valve 50 then occupies its wide open position.

The operating circuit 26 regulates the outlet pressure by means of the valve 16 and slaves the reference value to the leak resulting from the opening of the main check valve 50. The increase in the extent of opening of the main check valve 50 relative to its seating 56 causes a greater leak and therefore a drop in the pressure in the main conduit 14.

In the exhalation phase and in the closed position of the main check valve 50 of the flow regulating valve 16, the residual flow rate delivered by the fan 10 to the patient is of the order of about 10 milliliters per second and gives a residual pressure close to zero, of the order of 1 mbar.

The stability of the secondary check valve 52 in the exhalation phase is ensured by virtue of the presence of the openings 20 in the mask which allow a leakage flowrate from the mask substantially equal to the residual flowrate.

The openings 22 also make it possible to eliminate the flowrate peak at the beginning of the inhalation phase, which makes it possible to reduce barotrauma in the case of treatment of patients suffering from pathologies which obstruct the airways.

Figure 5:
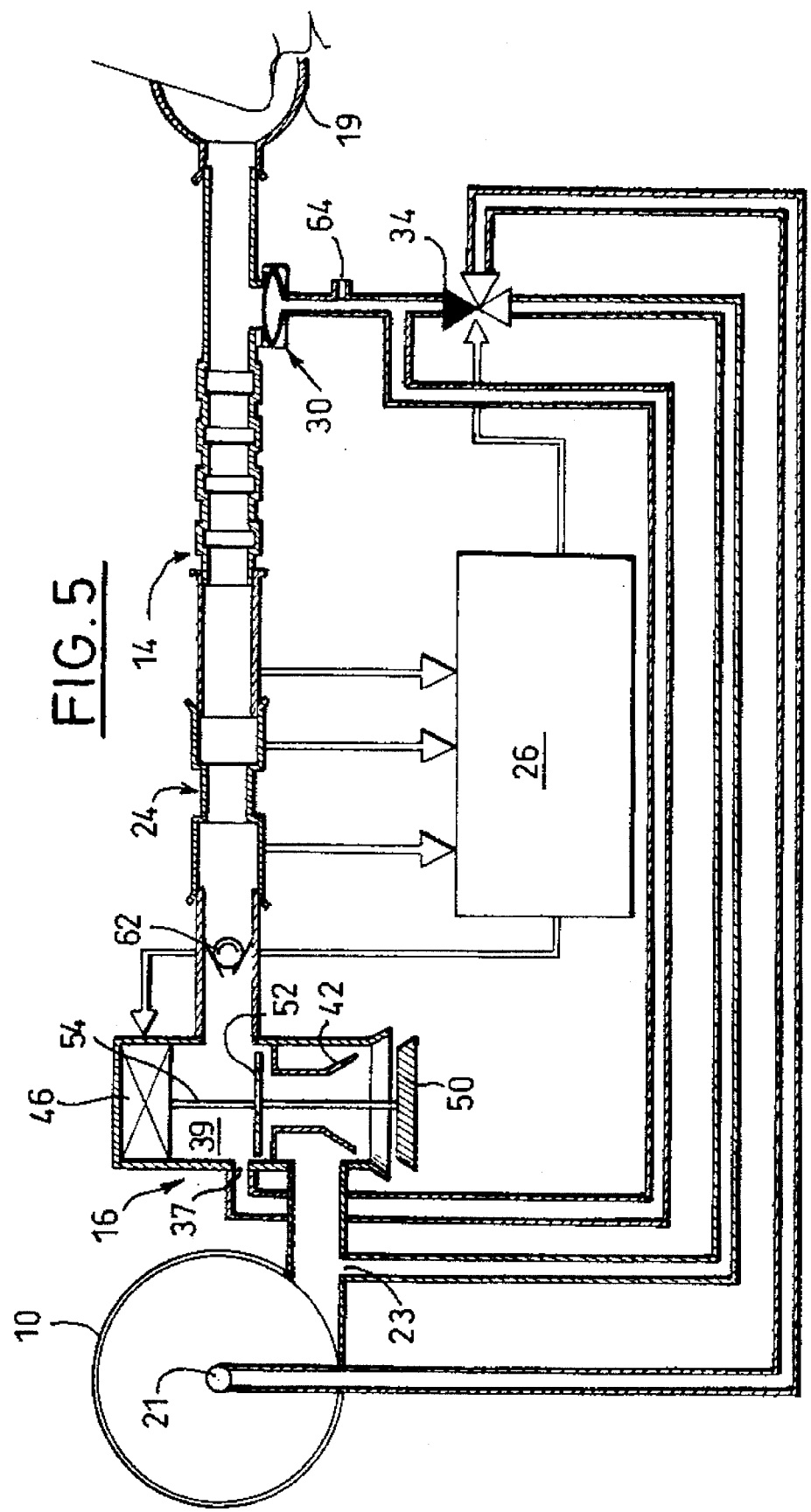
FIG. 5 is a diagrammatic view illustrating a second preferred embodiment of apparatus according to the invention and which is illustrated in an exhalation phase.

A second embodiment of the invention is shown in FIG. 5.

The elements represented in this figure, which are identical or similar to those represented in FIGS. 1 to 4, are denoted by the same reference numerals.

In this second embodiment, the face mask 19 via which the patient breathes does not have the ventilation openings.

However, various arrangements of the respiratory apparatus make it possible to conserve a relative pressure close to zero during the exhalation phase.

The regulating valve 16, which moreover retains the same operation as in the first embodiment, has a tubular baffle 42, the end of which has a conical shape like the mouth of a trumpet.

The pneumatically operated exhalation valve 30 from the previous embodiment is taken up again.

However, the distributor 34 is a double inlet model, one inlet being connected to the outlet 23 of the compressor 10, the other being connected to the air inlet 21 of the compressor 10.

Moreover, the exhalation valve 30 is permanently connected to a pressure tapping 37 in the outlet chamber 39 of the regulating valve 16.

Finally, a non-return check valve 62 is arranged in the main inhalation conduit downstream of the regulating valve 16 and upstream of the differential pressure flowrate sensor 24.

During inhalation, in order to maintain a reference pressure, the electromagnet 46 closes the main check valve 50, sending the flowrate of gas into an outlet chamber 39 of the regulating valve 16 and into the main inhalation line 14.

The pressure tapping 37 in the outlet chamber 39 of the valve 16 causes the exhalation valve 30 to close.

However, to prevent any undesirable leakage in the region of this valve, the distributor 34 is operated by the operating circuit 26 so as to deliver to the exhalation valve 30 the pressure taken from the outlet 23 of the compressor 10.

Complete closure of the valve 30 is thus ensured.

During exhalation, two operating methods especially are envisaged.

In a first operating mode, the electromagnet 46 causes the main check valve 50 to open and the secondary check valve 52 to close virtually completely, as was described previously.

However, the conical shape of the baffle 42 has the advantage of further reducing, through a venturi effect, the residual pressure in the outlet chamber 39.

The pressure tapping 37 in the outlet chamber 39 of the valve 16 therefore sends a pressure close to zero to the exhalation valve.

In addition, to ensure complete opening of the valve 30, the distributor 34 is operated so as to deliver to the valve 30 the partial vacuum tapped off at the inlet of the compressor 10.

Complete opening of the valve 30 is thus ensured, and exhalation can take place at an almost zero exhalation pressure.

The function of the non-return check valve 62 is especially to prevent contamination of the regulating valve 16 by the exhaled gases and prevent them from being reinhaled.

In a second embodiment, exhalation takes place at a non-zero exhalation pressure.

The distributor 34 is then closed and the exhalation valve 30 is subjected, for operating it, merely to the pressure prevailing in the outlet chamber 39 of the regulating valve 16, which pressure is regulated by the opening of the main check valve 50 depending on the pressure measured in the main inhalation conduit 14.

A small orifice 64 is moreover provided in the operating circuit of the valve 30 which determines a leakage flowrate in this circuit in order to ensure the stability thereof.

I claim:

1. An apparatus for assisting with the ventilation of a patient breathing in successive cycles, each of the cycles including an inhalation phase and an exhalation phase, said apparatus being of the type including an inhalation assistance mode, triggered by the patient during the beginning of the inhalation phase, which causes said apparatus to deliver to the patient a flowrate of gas under a pressure equal to a given reference value, said apparatus comprising:

a source of pressurized gas, said source including an outlet orifice which delivers a flowrate of pressurized gas;

a face mask for placing over the upper airways of a patient, whereby said face mask enables the patient to receive said flowrate of pressurized gas delivered from said outlet orifice of said source; and a transmission circuit for coupling said source to said said face mask, said transmission circuit including:

a main inhalation conduit coupled between said outlet orifice of said source of pressurized gas and said face mask;

a discharge orifice;

a secondary exhalation conduit for communicating with said face mask, said secondary exhalation conduit being coupled between said main inhalation conduit and said discharge orifice;

a flow regulating valve interposed in said main inhalation conduit, said flow regulating valve including means for maintaining a residual flowrate of gas substantially equal to a pressure of 1 mbar in said main inhalation conduit during the exhalation phase of each of the breathing cycles of the patient;

an exhalation valve interposed in said secondary exhalation conduit; and an operating circuit coupled to said flow regulating valve and said exhalation valve, said circuit operating said flow regulating valve based on the flowrate and pressure of said gas in said main inhalation conduit as measured downstream past said flow regulating valve in order to determine the beginning the inhalation phase of each of the breathing cycles of the patient, and said circuit causing said exhalation valve to open during the exhalation phase of each of the breathing cycles of the patient.

2. The apparatus according to claim 1, wherein said exhalation valve closes said secondary exhalation conduit until said operating circuit causes said exhalation valve to open said secondary exhalation conduit.

3. The apparatus according to claim 1, further comprising flowrate measuring means for measuring the flowrate of a gas flowing through said main inhalation conduit, said flowrate measuring means being interposed in said main inhalation conduit, said secondary exhalation conduit being coupled to said main inhalation conduit as a bypass in a location downstream from said flowrate measuring means.

4. The apparatus according to claim 1, wherein said source of pressurized gas includes a fan having a constant speed of rotation.

5. The apparatus according to claim 1, further comprising a differential sensor for measuring the flowrate of a gas flowing through said main inhalation conduit, said differential sensor being associated with said main inhalation conduit.

6. The apparatus according to claim 1, wherein said face mask includes at least one opening for venting the inside of said face mask to ambient air.

7. The apparatus according to claim 1, wherein said flow regulating valve includes a valve body which defines a regulating chamber, a first orifice selectively communicating with said regulating chamber to supply the pressurized gas thereto, a second orifice selectively communicating with said regulating chamber for delivering the pressurized gas in said regulating chamber to said main inhalation conduit, a third orifice selectively communicating with said regulating chamber for venting to ambient air, a moving member, a main check valve coupled to said moving member, and a secondary check valve coupled to said moving member, said moving member causing said main check valve to move from a first position which closes said third orifice to a second position which fully opens said third orifice and enables said pressurized gas to be vented therethrough to ambient air, wherein said secondary check valve is moved to a position which partially closes said second orifice when said main check valve is moved to said second position, in order to determine said residual flow rate under said pressure close to zero (0).

8. The apparatus according to claim 7, wherein said flow regulating valve further includes an actuating electromagnet coupled to said moving member, said actuating electromagnet being energized by said operating circuit.

9. The apparatus according to claim 7, wherein said flow regulating valve further includes an axial tubular baffle which reduces and shifts the noise spectrum resulting from the flow of gas towards the high frequencies.

10. The apparatus according to claim 9, wherein said baffle has a substantially conical end which generates a venturi effect during exhalation that allows the pressure of the residual flowrate to be reduced.

11. The apparatus according to claim 1, further comprising a distributor controlled by said operating circuit and wherein said exhalation valve is pneumatically-operated and supplied by said distributor.

12. The apparatus according to claim 11, wherein said source further includes an outlet where high pressure prevails and said distributor includes one inlet coupled to said outlet of said source and one outlet coupled to said exhalation valve, said distributor having an open and closed position.

13. The apparatus according to claim 11, wherein said source further includes an inlet where a partial vacuum prevails, said distributor includes two inlets and one outlet, one of said two inlets coupled to said outlet of said source and the other of said two inlets coupled to said inlet of said source, said outlet of said distributor coupled to said exhalation valve, said distributor having an open and closed position to one or the other of said two inlets.

14. The apparatus according to claim 13, wherein said flow regulating valve further includes an outlet chamber, said exhalation valve receiving, in parallel with said distributor, a pressure signal which comes from said outlet chamber of said flow regulating valve.

15. An apparatus for assisting with the ventilation of a patient breathing in successive cycles, each of the cycles including an inhalation phase and an exhalation phase, said apparatus being of the type including an inhalation assistance mode, triggered by the patient during the beginning of the inhalation phase, which causes said apparatus to deliver to the patient a flowrate of gas under a pressure equal to a given reference value, said apparatus comprising:

a source of pressurized gas, said source including an outlet orifice which delivers a flowrate of pressurized gas;

a face mask for placing over the upper airways of a patient, whereby said face mask enables the patient to receive said flowrate of pressurized gas delivered from said outlet orifice of said source; and a transmission circuit for coupling said source to said said face mask, said transmission circuit including:

a main inhalation conduit coupled between said outlet orifice of said source of pressurized gas and said face mask;

a discharge orifice;

a secondary exhalation conduit for communicating with said face mask, said secondary exhalation conduit being coupled between said main inhalation conduit and said discharge orifice;

a flow regulating valve interposed in said main inhalation conduit, for maintaining a residual flowrate of gas under a pressure of approximately zero in said main inhalation conduit during the exhalation phase of each of the breathing cycles of the patient, said flow regulating valve including a valve body which defines a regulating chamber, a first orifice selectively communicating with said regulating chamber to supply the pressurized gas thereto, a second orifice selectively communicating with said regulating chamber for delivering the pressurized gas in said regulating chamber to said main inhalation conduit, an axial tubular baffle which reduces and shifts the noise spectrum resulting from the flow of gas towards the high frequencies, a third orifice selectively communicating with said regulating chamber for venting ambient air, a moving member, a main check valve coupled to said moving member, and a secondary check valve coupled to said moving member, said moving member causing said main check valve to move from a first position which closes said third orifice to a second position which fully opens said third orifice and enables ambient air to be vented therethrough, wherein said secondary check valve is moved to a position which partially closes said second orifice when said main check valve is moved to said second position, in order to determine said residual flow rate under said pressure close to zero (0);

an exhalation valve interposed in said secondary exhalation conduit; and an operating circuit coupled to said flow regulating valve and said exhalation valve, said circuit operating said flow regulating valve based on the flowrate and pressure of said gas in said main inhalation conduit as measured downstream past said flow regulating valve in order to determine the beginning the inhalation phase of each of the breathing cycles of the patient, and said circuit causing said exhalation valve to open during the exhalation phase of each of the breathing cycles of the patient.

16. An apparatus for assisting with the ventilation of a patient breathing in successive cycles, each of the cycles including an inhalation phase and an exhalation phase, said apparatus being of the type including an inhalation assistance mode, triggered by the patient during the beginning of the inhalation phase, which causes said apparatus to deliver to the patient a flowrate of gas under a pressure equal to a given reference value, said apparatus comprising:

- a source of pressurized gas, said source including an outlet orifice which delivers a flowrate of pressurized gas, an inlet where a partial vacuum prevails;
- a face mask for placing over the upper airways of a patient, whereby said face mask enables the patient to receive said flowrate of pressurized gas delivered from said outlet orifice of said source; and
- a transmission circuit for coupling said source to said said face mask, said transmission circuit including:
  - a main inhalation conduit coupled between said outlet orifice of said source of pressurized gas and said face mask;
  - a discharge orifice;
  - a secondary exhalation conduit for communicating with said face mask, said secondary exhalation conduit being coupled between said main inhalation conduit and said discharge orifice;
  - a flow regulating valve interposed in said main inhalation conduit, said flow regulating valve including means for maintaining a residual flowrate of gas under a pressure of approximately zero in said main inhalation conduit during the exhalation phase of each of the breathing cycles of the patient;
  - a distributor controlled by said operating circuit, said distributor including two inlets and one outlet, one of said two inlets coupled to said outlet of said source and the other of said two inlets coupled to said inlet of said source, said outlet of said distributor coupled to said exhalation valve, said distributor having an open and closed position to one or the other of said two inlets;
  - a pneumatically-operated exhalation valve interposed in said secondary exhalation conduit, said exhalation valve being supplied by said distributor; and
  - an operating circuit coupled to said flow regulating valve and said exhalation valve, said circuit operating said flow regulating valve based on the flowrate and pressure of said gas in said main inhalation conduit as measured downstream past said flow regulating valve in order to determine the beginning the inhalation phase of each of the breathing cycles of the patient, and said circuit causing said exhalation valve to open during the exhalation phase of each of the breathing cycles of the patient.

* * * * *